(12) United States Patent
Preto et al.

(10) Patent No.: US 7,235,252 B2
(45) Date of Patent: Jun. 26, 2007

(54) METHOD OF PREPARING ORGANIC PEROXYACIDS

(76) Inventors: Andrea Preto, 10/A, Via Pineta, Sant'Anna d'Alfaedo-Corrubbio (Verona) (IT) 37020; Paolo Tabasso, 13, Via Piemonte, Peschiera d. Garda (Verona) (IT) 37019

( * ) Notice: Subject to any disclaimer, the term of this patent is extended or adjusted under 35 U.S.C. 154(b) by 750 days.

(21) Appl. No.: 10/448,101

(22) Filed: May 30, 2003

(65) Prior Publication Data

US 2004/0002616 A1 Jan. 1, 2004

(30) Foreign Application Priority Data

Jun. 3, 2002 (IT) .......................... VR2002A0062

(51) Int. Cl.
*A01N 25/00* (2006.01)
*C07C 409/24* (2006.01)
*C09K 3/00* (2006.01)

(52) U.S. Cl. .................. 424/405; 562/213; 252/183.12

(58) Field of Classification Search ...................... None
See application file for complete search history.

(56) References Cited

U.S. PATENT DOCUMENTS

| | | | |
|---|---|---|---|
| 5,077,008 A | 12/1991 | Kralovic et al. | 422/37 |
| 5,091,343 A | 2/1992 | Schneider et al. | 422/297 |
| 5,225,160 A | 7/1993 | Sanford et al. | 422/28 |
| 5,350,563 A | 9/1994 | Lindeman et al. | 422/28 |
| 6,514,509 B2 * | 2/2003 | Tabasso | 424/405 |
| 7,005,549 B2 * | 2/2006 | Hobson et al. | 568/30 |
| 2002/0004057 A1 | 1/2002 | Tabasso | 424/405 |

FOREIGN PATENT DOCUMENTS

| | | |
|---|---|---|
| DE | 286 370 A | 1/1991 |
| EP | 0 953 283 A | 11/1999 |
| WO | WO 94 18297 A | 8/1994 |

OTHER PUBLICATIONS

Block S S, "Disinfection, Sterilization and Preservation", Disinfection, Sterilization, and Preservation, Philadelphia, Lea & Febiger, US, pp. 172-181; XP002112246, 1992.

* cited by examiner

*Primary Examiner*—Sikarl A. Witherspoon
(74) *Attorney, Agent, or Firm*—Nixon & Vanderhye P.C.

(57) ABSTRACT

A system for a fast-rate preparation just before use of organic peroxyacids, in a hydroalcoholic environment, by mixing at temperatures lower than 40° C., preferably lower than 25° C., a first reactant and a second reactant, kept separate from each other during storage, to obtain an activated solution, the first reactant is in the solid or liquid state at a temperature from 5 to 45° C. and includes at least one acyl donating group, and the second reactant is in the solid state, at least in the temperature range from 5° C. and 40° C., and comprises a peroxide anion source in a concentration such as to provide at least 10-fold molar excess of peroxide with respect to the stoichiometric amount of the acyl-donor, a biocidal agent including at least one $C_1$–$C_{18}$ linear or branched aliphatic and/or aromatic alcohol, and a stabilizing buffer component suitable for keeping the second reactant at a desired pH value.

27 Claims, 4 Drawing Sheets

METHOD OF PREPARING ORGANIC PEROXYACIDS

FIELD OF THE INVENTION

The present invention relates to a method of preparing in situ organic peroxyacids stable with time in a hydroalcoholic solution, particularly indicated to be used in the health-care field (i.e. in hospitals, private clinics, dental surgeries, etc.) for carrying out cold-sterilization of medical-surgical devices, particularly the optical-fiber devices used for therapeutical and diagnostic applications.

In the present description and in the Claims, the terms listed below will be referred to their specific definitions given below.

GLOSSARY

Detergent: Agent that decreases surface tension between organic dirt and a surface to be cleaned, so as to assist in the removal of dirt.

Acyl donor: A compound having the following general formula: $R^1$—CO—L, where L is a leaving group and $R^1$ is an alkyl, aralkyl or aryl group, each group having up to 24 carbon atoms and being either substituted or non-substituted.

N-acyl donor: A compound responding to the above description, where L is a leaving group bonded to carbonyl carbon through a nitrogen atom.

O-acyl donor: A compound responding to the above description, where L is a leaving group bonded to the carbonyl carbon through an oxygen atom.

HLB (hydrophilic-lipophilic balance): An arbitrary parameter used to categorize surfactants on the basis of a relative ratio of polar functional groups to apolar functional groups in the molecules of the surfactant. Sometimes, this value is determined experimentally, e.g. by Reverse Phase Chromatography. There are numerous methods of reckoning HLB.

On the basis of the HLB value, surfactants are classified as:
  a) HLB from 1 to 3.5: anti-foaming,
  b) HLB from 3.5 to 8: W/O (water in oil) emulsifiers,
  c) HLB from 7 to 9: cleaning and dispersing agents,
  d) HLB from 8 to 16: O/W (oil in water) emulsifiers,
  e) HLB 13 to 16: detergents,
  f) HLB from 14 to 40: solubilisers.

Disinfectant: An agent that reduces the risk of infections; it is usually chemical in nature, destroys pathogenic germs, and any other type of harmful micro-organisms through a non-specific and non-selective mechanism of action. The term is to be referred to substances used on inert materials (e.g. medical devices, surfaces and other items).

Germicide: A physical or chemical agent that destroys micro-organisms, particularly pathogenic micro-organisms. The term as usually used is associated with the suppression of all micro-organisms causing infections, although as for the word "disinfectant" similar to it, it does not necessarily encompass bacterial spores. Germicides are usually applied both onto living tissues and inanimate items.

Bactericide: An agent that suppresses bacteria. The difference with a germicide lies in that it does not destroy mycetes, viruses and other micro-organisms other than bacteria in their vegetative form.

Fungicide: An agent that suppresses mycetes. As compared with the term "bactericide" its action on spores is not to be ruled out, and thus its use could result in mycotic spores being suppressed.

Virucide: An agent, often a chemical agent, that destroys or inactivates viruses.

Tubercolicide: An agent, often a chemical agent, that suppresses acid-resistant bacilli (*Mycrobacterium tubercolosis*) exhibiting a greater resistance to disinfectant agents.

Sporicide: An agent, often a chemical agent, that destroys bacterial spores. The term is commonly referred to substances that are applied onto inanimate items. Since spores are forms of micro-organisms that endure unfavorable environmental conditions, a sporicide is a sterilizing agent.

Biocide: An agent that kills pathogenic and non-pathogenic living organisms. In so far as the present description is concerned, the term is to be referred to in its widest meaning. It includes suppression of all microbial agents, regardless of their type. Thus, the term "biocide" refers to all virucide, algicide, sporicide, bactericide, fungicide, tubercolicide, etc. activities.

Contamination: Transitory presence of an infective agent on a body surface, on clothing, tools or other inanimate items.

Decontamination: Suppression of any microbial contamination so that tools and items thus treated are made safe for subsequent use. This process comprises disinfection at a different level from sterilization.

Sterilization: A physical or chemical process where all forms of life, including bacterial spores, are destroyed or eliminated. It is the highest level of microbial suppression. If a process does suppress bacterial spores on a routine basis, then one commonly assumes that the process can suppress any other micro-organism, thus obtaining sterilization.

Disinfection: A less lethal process as compared with sterilization. It virtually eliminates all pathogenic micro-organisms, but not necessarily all their microbiological forms (e.g. endospores).

High level disinfection: A process where chemical disinfecting agents with sporicidal activity are used for prolonged contact times. A high level disinfectant can become a cold sterilizing agent if it exhibits a sporicidal activity at ambient temperature and for a reasonably short contact time, compatible with the disinfection conditions applied in the health-care field.

Intermediate-level disinfection: A process where chemical disinfecting agents are used that do not necessarily comprise those suitable for suppressing large amounts of bacterial endospores in relatively short times, but rather those suitable for inactivating *tubercolosis* bacillum that is more resistant than common vegetative bacteria to the action of liquid germicides. An intermediate level disinfectant is also active against small and medium size fungi and viruses with or without lipoprotein sheath.

Low-level disinfection: a process where chemical disinfecting agents, suitable for quickly suppressing living forms of bacteria and fungi, as well as medium size viruses provided with a lipoprotein sheath, are used.

Medical devices: Medical tools, equipment and apparatuses whose use entails a significant risk of transmitting an infection to patients or health-care personnel. Accordingly, these items are to be sterilised or disinfected in order to prevent cross-contaminations and infections from taking place.

In order to understand the nature of said disinfection, it is now appropriate to divide medical devices in three general categories, on the base of the risk of infection connected to their use.
(See the following table).

| Type of items | Definition | Example | Type of decontamination |
| --- | --- | --- | --- |
| Critical (high risk) | Items directly introduced into the human body (blood or normally sterile regions) | scalpels, tweezers cardiac catheters prostheses side of artificial organs wetted by blood | Sterilization High level disinfection (thermolabile items) |
| Semicritical (average risk) | Items that normally contact intact mucous membranes, not affecting their continuity | flexible optical fibers endotracheal tubes and aspirators urinary catheters | Sterilization (desiderable) High level disinfection Intermediate level disinfection |
| Not critical (low risk) | Items that are not directly brought into contact with the patient or, if this happens, only with integral skin | face masks humidifiers walls, floors surfaces of the reunited | Low level disinfection |

BACKGROUND OF THE INVENTION

In the field of washing and bleaching fabrics, the use of a combination of a hydrogen peroxide precursor (perborate tetrahydrate and percarbonate) and an O-acyl activator (e.g. pentaacetylglucose) and an N-acyl donor (e.g. tetraacetylenediamine) in the same or in different compositions is known. Once dispersed in water, these components react with each other to form the peroxyacid anion. This reaction occurs in a strictly aqueous environment and at an invariably alkaline pH (pH>9). Peracid anions are instantly released upon mixing the two components with water that can have been heated to a greater or a lesser extent. Peroxyacid stability in this environment is limited to the point that the solution cannot be reused for an effective bleaching and disinfection process.

In these formulations, the activator and the peroxide source do not react with each other during storage, and are both stable under the usual storage conditions (temperature not higher than 40° C.). Several proposals have already been suggested (see e.g. WO-A-9213798) according to which, the N-acyl and the O-acyl donors are covered with or aggregated by solid organic acids such as citric, lactic and glycolic acid, so that a longer storage duration is obtained. Other proposals aim at using acylated citrate esters (see WO-A-93167), or N-acyl lactams and other acyl donors. Independently from the use and the activating species, all the above prior art proposals have the following features in common:

they react in an alkaline environment;

they form peroxyacid anions in situ;

the dilute solution is immediately used as a bleach and/or disinfectant;

limited stability of the solutions with time, owing to the degradation of hydrogen peroxide being promoted in an alkaline environment (with consequent release of oxygen), which, in turn, results in the reaction equilibrium of the peracetic acid reaction being shifted back leftwards, yielding to a decrease in its concentration (see the reaction diagram shown below):

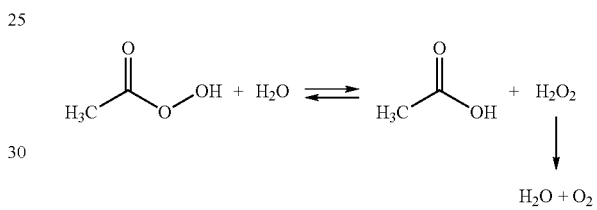

Conversely, an acidic environment clearly promotes greater stability with time of both the hydrogen peroxide, and the peracid. All commercially available concentrated and diluted solutions based on hydrogen peroxide and peroxyacids have an acidic pH for this reason, for the very reason of preserving their characteristics for the longest possible time in standard storage conditions.

It is also well-known to the skilled person in the art that organic peroxyacids can be used as strong oxidizing agents for a wide variety of oxidation reactions that occur in up to (quantitatively) high yields. In many reactions for preparing these peroxyacids (see in particular "Organic Peroxides" volume 1, Ed. D. Swern, Wiley Interscience (1970) 313–335) the carboxylic acid or anhydride, or their most reactive acyl chloride or aldehyde are used as a starting material for a perhydrolysis reaction caused by hydrogen peroxide.

GB-A-931,119 describes for instance a process for producing the peroxyacid by means of the hydrogen peroxide reaction with an ester of the organic carboxylic acid, in the absence of water and in the presence of a minimum quantity of a strong inorganic acid that acts as a catalyst. This process requires that the hydrogen peroxide be dissolved in liquid ester, that water be removed and that the acid catalyst be added only upon complete removal of water.

Moreover, anhydrous processes for producing aliphatic or aromatic percarboxylic acids have been proposed. DE-3638552 discloses an innovative apparatus for the production of percarboxylic acids on an industrial scale. All these methods are special processes useful for a synthesis on a laboratory or industrial scale, but certainly not for use in the health-care, household environments or in general. Some starting reagents are in fact very dangerous, and thus they can be handled only by specialized personnel each equipped with suitable protective clothing. Other starting materials, such as acetic anhydride, are sensitive to water because of their high reactivity, and thus need to be stored under special conditions.

With reference to the detergent formulations used for bleaching fabrics, Croud et al., (WO 94/18297) have proposed a system having the same advantages as those of bleaching combinations, but where the reaction between precursor (peroxide source) and activator and/or the subsequent oxidation step is carried out under acidic conditions and at relatively low concentrations. The reaction is carried out in a typically aqueous environment at a pH lower than 6.5. Moreover, in the several Examples set forth in WO94/18297 formulations are disclosed, in which both active components (peroxide source and activator) are in solid form under given storage conditions as a single composition or as separate compositions, and thus need a third liquid component (water) so that their reaction can take place. In the same document, various concentrations of hydrogen peroxide are provided up to a maximum of 60% w/w. Even the operating temperature can vary up to a maximum of 95° C. In the formulation, there is provided a component releasing an acidic species, or suitable for reacting with a by-product of the perhydrolysis reaction for decreasing pH and maintaining the solution at a pH lower than 7. Such a component can be present as a single composition together with the activator, and be a polyol, an organic polycarboxylic acid, boric acid and sodium di-hydrogen phosphate. The formulation can also comprise a surfactant. The presence of the last component is to be ruled out in washing operations in washing-machines involving shaking, since an excessive amount of foam would be produced, and thus the washing machine would discontinue its operation.

In WO 96/18297 a typically solid biocidal composition is disclosed, which contains a peracetic anion generating system mixed with a stabilizing organic acid (citric acid, succinic acid) selected for its ability, when this composition is added to an aqueous solution at suitable concentrations, to control peracetic ion release into such aqueous solution with time. The relative ratios between the components of the generating system, on the one hand, and the stabilizing organic acid, on the other, are adjusted so that the concentration of the generated peracetic acid is higher than a concentration threshold above which it can induce a biocidal effect for a predetermined time length of action, e.g. longer than 24 hours.

The composition disclosed by the above prior art document is in solid form and substantially based on three components:

$H_2O_2$ and/or generator of peroxides, e.g. persalts, such as perborates, persulphates, percarbonates, products whose properties as activators of O-acyl and/or N-acyl donating bleaching compositions of the TAED type (tetraacetylethyldiamine, acetylated sugars or other compounds of this type disclosed in the references of the state of the art);

organic polycarboxylic acid, such as citric acid and succinic acid.

Such a solution, once dispersed in water, yields peracetic ions as a disinfecting active principle with a long-lasting action.

U.S. Pat. No. 5,350,563 (Kralovic et al.) discloses a powdered formulation in which, regardless of whether they be stored in two or three compartments, to react with one another, the various components in the solid state are mixed in water, that makes up a further component. In Kralovic's method a (solid) perborate stored in one compartment is used as an active oxygen source, whereas a (solid) TAED acetylating agent is stored in the other. The compartments can also contain compositions in the solid state, such as a buffer system for controlling pH, corrosion-preventing materials, surfactants, sequestring agents and the like. However, the different components must always be dissolved in a liquid solvent and according to a very precise addition sequence, owing to higher or lesser susceptibility of the N-acyl and/or O-acyl donors to inactivation triggered by hydrolysis. Kralovic's powdered mixture was actually already known to the skilled persons in the art since it had already been widely used as a bleach for fabrics. Kralovic disclosed that the use of fast-rate and slow rate acetylating agents in a 1 to 1 molar ratio in powdered mixture makes it possible to obtain a solution with a more stable peracetic acid concentration of 2000 ppm. The fast-rate acetylating agent, that] in the above cited Examples corresponds to TAED (tetraacetyldiamine) is so defined since, the other conditions (pH and solution temperature) being equal, it undergoes an attack by peroxide ions at a fast rate.

The slow rate acetylating agent (acetyl salicilic acid in the above cited Examples) on the other hand undergoes a slower rate and delayed perhydrolysis, and thus it contributes in keeping the concentration of the initially formed peracetic acid stable with time in the solution. This too, like the previous composition disclosed by WO 96/18297, is a composition that, once dispersed in water, yields to a biocidal solution based on peracetic acid that is stable with time.

In U.S. Pat. No. 4,900,721 (Bansemir et al.) the synergistic biocidal effect obtained by combining hydrogen peroxide or peracids with alcohols is disclosed.

In other words, the association of alcohols, on the one side, and organic peroxyacids and hydrogen peroxide, on the other, proposed by Bansemir, has a biocidal effect that is too limited to meet the requirements of the high level disinfection typical of the health-care field.

The preparation of peracetic acid in situ by reaction of hydrogen peroxide with peracetic anhydride and/or acetic acid in the presence of an inorganic acid catalyst is used in agriculture for carrying out controlled disinfection of hydroponic seedings as disclosed in EP-0 361 955. In fact, such method makes it possible to significantly reduce the risks associated with shipping and subsequent handling of concentrated peracetic-acid-based solutions. Such solutions are in fact corrosive and combustive, and thus, when preparing diluted solutions starting from said solutions, strict handling precautions must be adopted.

EP-0 12 781 discloses the use of O-acyl donor compounds and organic acids for the production of their respective peroxyacids by a catalyzed acid and base perhydrolysis reaction. Such compositions containing these activators are used for cleaning, bleaching and disinfecting fabrics.

U.S. Pat. No. 5,279,735 discloses dyes that are stable to oxidation and thus can be used to dye organic peroxyacid-based solutions over a predetermined period of time.

EP-0 953 283 (Farmec) describes a two-component system for preparing a peracetic acid based hydroalcoholic solution in situ. Such a system is, however, affected by some limitations substantially due to the following:

the system is not always adequately stable with time and provides for an N-acetyl and O-acetyl donor being dissolved in an aqueous environment, the donor undergoing degradation, particularly at relatively high temperatures (such as those reached in summertime);

no buffer system is provided in the parent solution that is suitable for simultaneously obtaining an effective and fast activation and a biocidal activity over a prolonged period of time.

BRIEF DESCRIPTION OF THE DRAWINGS

The invention is further described with reference to the attached drawings in which.

SUMMARY OF THE INVENTION

Figure 1:
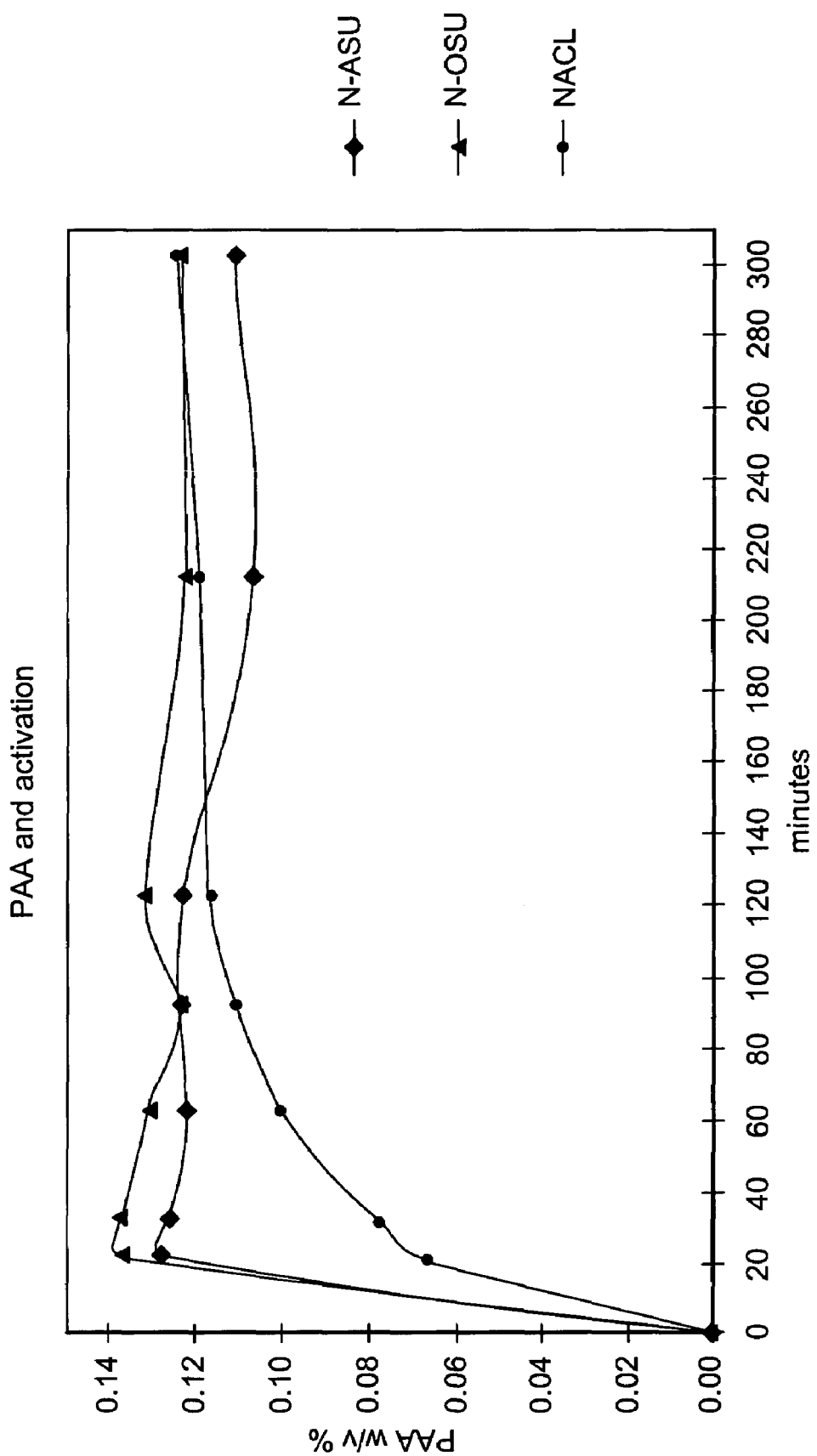
FIG. 1 is a graph relating activation of peracetic acid (PAA) by three N-acyl donors over time.

The main object of the present invention is to produce an oxidizing species in situ (just before being used) based on an organic peroxyacid in a hydroalcoholic solution at such a concentration above a minimum threshold level that full biocidal activity, including sporicidal activity, is provided.

Another object of the present invention is to obtain a hydroalcoholic solution containing peracetic acid and hydrogen peroxide, having an enhanced biocidal activity that lasts over a sufficiently long period of time. In some fields of application, mainly in surgery, it is absolutely necessary, in fact, that hospital workers, whether doctors or paramedics, are assured about the disinfecting and/or sterilizing effects of the solutions they use, without having to worry (of course, within predetermined time intervals) about whether the activity still persists or not, also bearing in mind that the same can be used repeatedly.

These and other objects, which will be better apparent from the following description, are attained by a system according to the present invention for preparing organic peroxyacids in situ or just before use in a hydroalcoholic environment at a fast rate, by simply mixing at temperatures lower than 40° C., more preferably at a temperature lower than 25° C., an activator or first reactant with a second reactant or parent solution, which are kept separate from one another during storage, in order to obtain an activated solution, wherein:

said activator is in the solid or liquid state at a temperature from 5° C. to 45° C., is lipophilic, and includes at least one acyl-donor, and said second reactant is in the liquid state, at least in the temperature range from 5° C. to 40° C., is hydrophilic, and includes a peroxy anion source at such a concentration that at least a 10-fold molar excess of peroxide is provided, with respect to the stoichiometric amount of said at least one acyl-donor, a biocidal agent comprising at least a $C_1$–$C_{18}$ linear or branched chain aliphatic and/or aromatic alcohol, and a stabilizing component also acting as a buffer, which is designed to keep the parent solution at the desired pH.

By simply mixing/combining the said second reactant or parent solution with the said first reactant or activator, a hydroalcoholic solution is obtained, which has the following main properties:

1) fast hydrogen peroxide or peroxy anion formation (within 15–30 minutes from mixing the two generator-activator components) following hydrogen peroxide or peroxy anion attacking the acylic donor present in the activator;

2) stable dying of the activated generator with time (additivated with the activator) owing to the presence in the activator of a dye selected from most stable due to the bleaching action by organic peroxides;

3) progressive pH reduction in the solution while gaining as a consequence greater stability in the organic peroxyacid, and thus keeping its concentration above the threshold level;

4) presence in the hydroalcoholic solution of a strong excess of hydrogen peroxide with respect to the stoichiometric concentration at equilibrium;

5) presence of a $C_2$–$C_{16}$ aliphatic and/or aromatic alcohol with a well-known biocidal activity;

6) fast-rate bactericidal, fungicidal, tubercolicidal, virucidal and sporicidal activity (within 30 minutes of contact time) according to all European standards in connection with antimicrobial efficacy as provided for in European standard NF T 72-190 (carrier test) carried out in the presence of a dried organic material (dried milk);

7) keeping the properties listed above, thereby ensuring biocidal activity for a long period of time (from 7 days to 2 months) depending upon whether the solution is used for a chemical sterilization to be carried out manually (by simply dipping the medical-surgical devices into it) or automatically (i.e. by means of mechanical equipment that strongly shakes the solution for a greater and more intimate contact thereof with the item to be sterilised).

According to the present invention, two distinct steps are provided:

Step 1: Fast-rate production in situ of a hydroalcoholic solution containing peracetic acid (this term is meant to indicate any $C_2$–$C_{16}$ aromatic and/or aliphatic percarboxylic acid) at a given concentration, and hydrogen peroxide in such an excess with respect to its stoichiometric amount that a fast acting biocidal effect is provided (within 30 minutes);

Step 2: Use of the solution thus prepared for a whole range of high level cold disinfection and/or sterilization processes of surfaces, medical-surgical devices, (particularly thermosensitive apparatuses, e.g. endoscopes), dental prostheses, as well as for other applications for which such a sterilizing effect is required that cannot be obtained by means of ionizing radiations, sterilization with ethylene oxide or dried or wet heat sterilization.

This use can also entail the use of tool or endoscope washing machines, in which the hydroalcoholic solution is strongly shaken, particularly because it is sprayed or pushed, and thus undergoing an accelerated degradation.

In brief, according to the present invention, a fast rate production in situ of organic peroxyacids in a hydroalcoholic environment is carried out at a temperature lower than 40° C., preferably lower than 25° C., by simply mixing only two components that remain separated during storage. The main properties of these compounds are as follows:

Parent solution—Generator: It is the second reactant or component present in greater quantity than the other (first) component. Such component must:

a) be always in the liquid state in the temperature range from 5° C. to 40° C.;

b) be always hydrophilic;

c) contain a peroxide anion source (e.g. hydrogen peroxide), d) have a peroxide source concentration expressed as a hydrogen peroxide % w/w concentration ($H_2O_2$:MW 34.02) such that it is harmless to a professional user, and thus ranging from $0<H_2O_2\%$ w/w$<5$; this concentration must always be such that a great molar excess of peroxide with respect to the stoichiometric amount of the acyl-donor component is provided.

e) contain a peroxide stabilizer, particularly one selected from widely used and well-known phosphonic acids and conjugated salts thereof, which, besides the stabilizing effect in itself, makes it possible to have a buffer system for the solution at the desired pH. This phosphonate/phosphonic acid system is present in such an amount that the peroxide concentration in the solution is kept stable while being stocked at temperatures lower than 40° C.

Since peroxide is present in large excess with respect to the stoichiometric amount of the other component, a concentration decrease up to 10% w/w of the initial value is permissible (e.g. initial value=4.5% w/w, permitted minimum value=4.05% w/w at the end of the rated storage time). In order to ensure all this, more stringent storage conditions can be applied, that should be applicable, however, to a household or healthcare environment, e.g. temperature <30° C. As a matter of fact, it is known that all organic and inorganic peroxides are more stable, the lower their storage temperature, the pH value of the solution are and the fewer impurities they include (see: "Disinfection, Sterilization and Preservation", fourth edition—Seymour Block; page 176).

f) have a stable pH and above 6.50 at 20° C. for the whole rated storage time;

g) guarantee the pH value given above by means of a phosphate and/or phosphonate buffer system in such an amount as to ensure that the pH value is kept constant in the parent solution before activation, and "physiological" lowering of pH after activation (addition of the activator), and progressive organic peroxyacid formation can take place, thereby allowing the solution eventually to stabilize itself at greater stability conditions. A pH value of the parent solution greater than 6.50 is required to attain production of organic peroxyacid within short intervals of time compatible with the healthcare effectiveness (20–30 minutes) at a % w/w concentration greater than the biocidal activity threshold level.

As it is known to a person skilled in the art that the faster the perihydrolysis of an O-acyl and/or N-acyl donor is, the higher the pH value of the solution (compatibly with the hydrogen peroxide stability which is degraded under basic conditions owing to dismutation phenomena, thus releasing active oxygen). It is also true that the peroxide initially rapidly formed in the solution remains stable the more so the greater the extent at which the solution then becomes acid. This is what spontaneously happens within the parent solution in the minutes following activation, owing to the carefully adjusted amount of the buffer system used, depending on the concentration of the binary "peroxide source/activator" system and thus on the concentration of peroxyacid that is formed in the solution;

h) always contain an aliphatic and/or aromatic $C_2$–$C_{18}$ linear or branched chain alcohol having a recognized biocidal effect and at a concentration in the range from 9.00 to 70.00% w/w. Such alcohol accomplishes a double function: i.e.

enhancing or, better, speeding up the biocidal effect exerted by the organic peroxide together with a strong excess of hydrogen peroxide;

making it possible to reduce the concentration of organic peroxyacid to obtain the same biocidal effect, thereby reducing the potential risk of corroding particularly sensitive apparatuses, especially when the same sterilizing solution is used repeatedly.

Activator: it is the first component or reactant present in a smaller amount and fulfilling the following requirements:

a) Being in the liquid or solid state at a temperature of 25° C.

b) Containing one or more O-acyl and/or N-acyl donors. Such donors can be distinguished, other conditions being equal, depending on quick or slow rate at which they undergo perhydrolysis reaction.

c) Given the particular sensitivity of these activators to water or air moisture, they should never contact water both during activator preparation and subsequent storage.

d) For this reason all activating formulations are lipophilic (fat lovers) and can contain, if in the liquid state, a dispersing component, e.g. a non-ionic surfactant and/or solvation agent, e.g. a glycol ether, in effective and sufficient amounts. The amounts of these two components can vary depending on the amount of activator to be dispersed in the parent solution. However, any component designed to contact the acyl-donor must include no water to ensure the activator preservation with time.

e) The amount of acyl-donor in the formulation can freely vary in the range from 0.01% to 100.00% depending on the % w/w of peracid to be obtained and on the parent solution to activator ratio.

f) The activator can contain an alcohol as a solvent or dispersant. Such alcohol must be possibly a long-chain branched alcohol to avoid any nucleophilic attack by alcohol itself to the acyl bond of the acyl; its concentration in the formulation can vary in the range from 5.00 to 50.00% w/w.

g) The agent suitable for promoting dispersion of the lipophilic activator (as fine droplets) in the hydrophilic parent solution must be a non-ionic surfactant (e.g. ethoxy alcohol, Tween-sorbitan monolaurate series, monooleate, polyethoxy monostearate) having a HLB value higher than 10, and thus suitable for enhancing formation and stabilization of o/w (oil in water) liquid emulsions. Its concentration may range from 0.01 w/w % to 5.00 w/w %. When the activated solution is be used in automatic machines, this component should be kept at a low concentration to prevent frothing effects that could hinder the sterilization process.

h) A solvating agent suitable for promoting solubilization of the lipophilic acyl donor in a hydrophilic environment of the parent solution is a glycol ether, e.g. hexylene glycol, diethylene glycol monohexyl ether, tripropylene glycol methyl ether $CH_3O[CH_2CH(CH_3)O]_3H$, and so forth. Its concentration in the activating formulation can range from 0.01 to 5.00 w/w %.

i) Finally, the formulation may or may not contain a dye or pigment selected from those disclosed in U.S. Pat. No. 5,277,735 that have both some resistance to the bleaching effect exerted by organic peroxyacids over a given time interval, and a good dispersion ability in a liquid lipophilic environment or, in solid form, in the activators used in the solid state. The main function of this dye is to be a useful visual witness of completed activation (mixing of the generator with the parent solution) and thus formation of a peroxyacid, with no need of any analytical test. All this is particularly useful in the healthcare field, since coloring of the parent solution is an immediate indication to the operator that activation has taken place. Although the use of such dyes was already disclosed by Louis C Cosentino in 1991, the application of the same dyes for performing the function provided for in the present description appears to be entirely novel.

The main object of the present invention is thus to obtain, by simply mixing the two components described above, a hydroalcoholic solution where organic peroxyacids and their respective anions are quickly formed in situ, so as to quickly overcome (within 20–30 minutes from mixing) a minimum threshold concentration level above which a biocidal effect in its wider meaning is provided. This solution having a neutral or a slightly acidic pH in its initial stages, owing to the features of the buffer system used, in the next following minutes stabilizes itself at such acidic pH values (4.00–4.50) that a greater stability both of the hydrogen peroxide and the formed peroxyacid is obtained. Such system could be referred to as a "living system" that, unlike those suggested in state of the art, initially has a suitable environment for quick activation (at neutral or slightly basic or acidic pH, and in any case >6.50, as is typical for the solid compositions used for bleaching and deterging fabrics) and subsequently, although in an independent way and without adding any component, it shifts to an acidic environment that better provides for keeping it as a sterilizing solution for extremely long time intervals never achieved or achievable before, i.e. from 7 to 60 days depending on its specific use.

Over this time interval a full biocidal action is provided, mainly owing to the ternary peracetic acid-hydrogen peroxide-/alcohol (e.g. ethyl, propyl, isopropyl, methyl alcohol), the hydrogen peroxide being in excess of its stoichiometric amount.

Owing to such acquired outstanding ability of lasting long, sometimes it can be used for automated cold chemical sterilization, which is in fact an extremely critical process since the solution easily and quickly degrades owing to excessive shaking which it is subjected to.

The same solutions formulated and produced according to the present invention have significant differences in stability when used in static conditions in a vat as compared with their use in dynamic conditions such as in a washing machine. By way of example, a solution stable under static conditions for 60 days, can hold out 12 consecutive days when used in a machine at an average 10 cycles per day.

Once the present invention has been set forth, the differences and the innovation level attained by it with respect to the prior art should also be better apparent.

The present invention takes advantage of the concept of preparing organic peroxyacids in situ, typically in powdered formulations initially used for bleaching and deterging fabrics. The present invention is also aimed at solving problems faced in connection with storage and handling of concentrated or ready for use solutions based on organic peroxyacids both in the healthcare and in the household and/or industrial fields.

However, with respect to the prior art, the present invention attains a further and decisive advantaged and improvement of the process, mostly in terms of stability depending on the prevailing field of use, i.e. that of frequent and repeated cold chemical sterilization of critical and semi-critical medical-surgical devices which are used for diagnostic and/or therapeutic purposes and cannot be regenerated otherwise between operations on different patients, mostly owing to their being heat sensitive.

The fact of providing a simple two-component system that simply by mixing makes it possible to obtain a biocidal solution that is extremely stable over repeated utilizations and has a sure sterilizing effectiveness provides for a decisive improvement above all in the healthcare field.

EXAMPLES

Search work was initially directed towards finding out the best N-acyl and/or O-acyl activator of all those available and disclosed in the prior art referred to above. The features sought for in this initial search were:

a rapidly acting acylating agent (i.e. provided with an electrophilic carbonyl carbon) suitable for causing a perhydrolysis reaction due to electron-withdrawing effect on the carbonyl carbon and for providing a sufficiently high concentration of its respective peracid within short times (20–30 minutes) for the specified objects;

a good conservation under standard storage conditions (at temperatures ranging from 20° and 40° C.).

an ability to yield after activation an activated solution in which the organic peroxyacid concentration is as stable as possible.

The following five acetyl donating compounds were assessed at the outset:
1. N-acetoxysuccinimide
2. N-acetylsuccinimide
3. N-acetylcaprolactam
4. N,N,N,N-tetraacetylethyldiamine (TAED)
5. N,N,N-triacetylethylenediamine
6. Pentaacetylglucose Among these five compounds, only N-acetylcaprolactam is in the liquid state at ambient temperature. Some of the compounds are available on the market, although it was possible to carry out their synthesis by method available in the state of the art.

From a preliminary assessment, it was observed that:

Although poorly soluble in water, the first two compounds rapidly undergo perhydrolysis, once dispersed in a hydroalcoholic solution based on 3% w/w hydrogen peroxide; however, by being very reactive, they are highly sensitive to air moisture, so much so that their storage requires too severe conditions for use and above all for standard shipping.

The third compound tends to separate at the bottom, once dispersed in a hydrophilic environment; however, it dissolves in the few moments after mixing owing to advancement of the perhydrolysis reaction and the solubilization of the reaction by-products. This compound is also to be regarded as a medium fast rate N-acetylating agent and does not cause any particular problem, if suitably stored in tight-sealed vessels.

The fourth compound is very well-known in the field of decontaminating, detergent and bleaching formulations and is a fast-rate acetylating agent even though it exhibits little solubility in water, particularly at ambient temperature and when the solution has a neutral-acidic pH.

Finally, the fifth and the sixth compounds from a preliminary assessment were found to be weak acetylating agents and also poorly miscible with water.

Further evaluation aimed at ascertaining the actual concentration of peracetic acid formed in the parent solution was limited to the first three compounds listed above.

Figure 2:
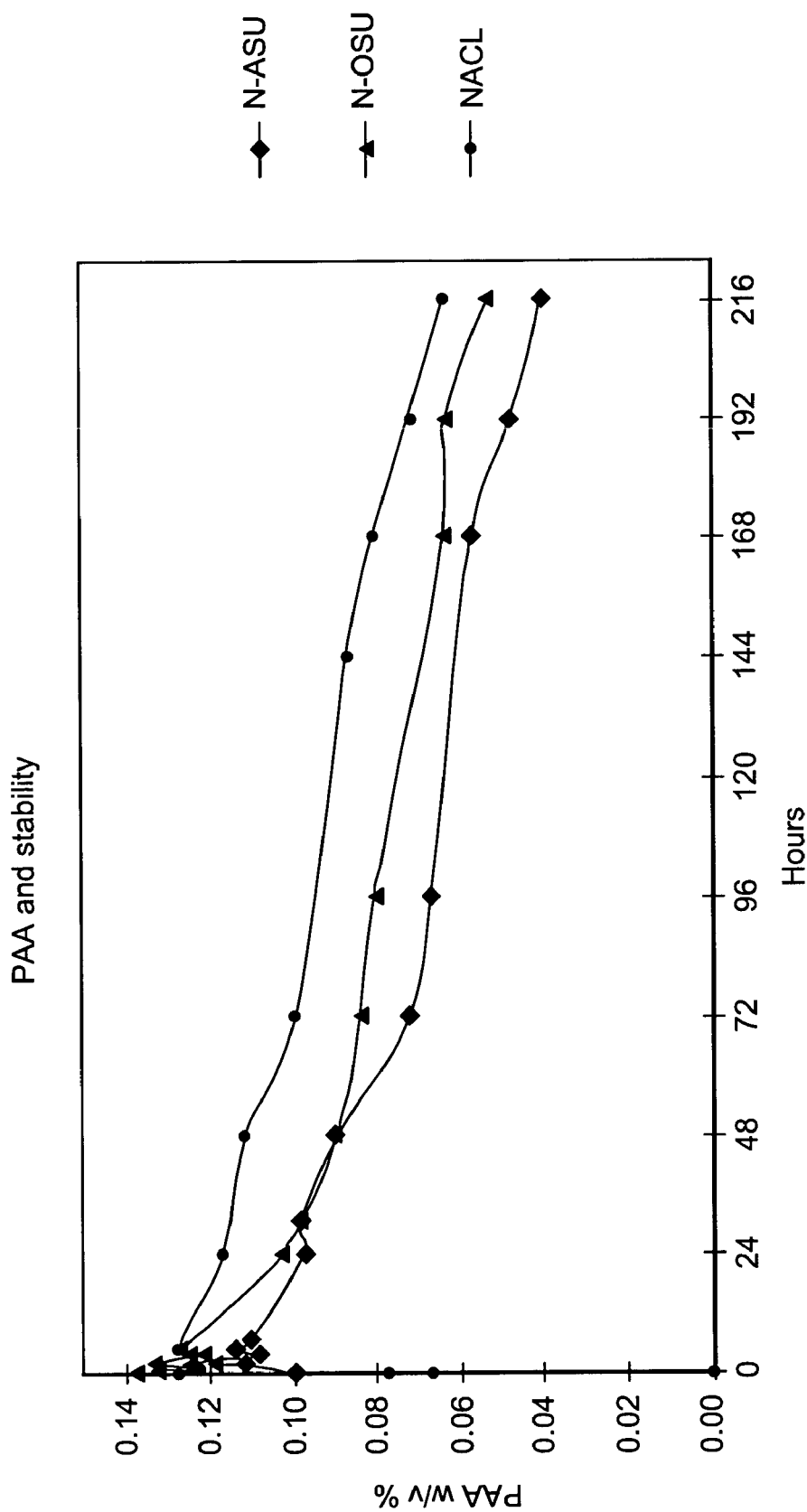
FIG. 2 is a graph relating PAA stability to the same N-acyl donors over time.

The other conditions (temperature, humidity, generator composition) being the same, equimolar amounts of the three N-acyl donors were dispersed in the parent solution to determine the formation rate of peracetic acid in the solution and the stability with time of such a concentration. The method adopted for quantitative determination of organic peroxyacid in the presence of a large excess of hydrogen peroxide (in this and in the following tests) was a sequential double-titration, the first of which is a permanganometric test designed to titre and eliminate any hydrogen peroxide in excess, and this was immediately followed by an iodometric titration to determine the concentration of the remaining organic peroxide. The results are shown below, both as activation rate (see FIG. 1), and stability of the peracetic acid concentration (see FIG. 2) are concerned.

As it can be seen, at the activation level (FIG. 1) as it could be expected, the most reactive compound was N-acetoxysuccinimide (N-OSU) that also had poor stability with time. An intermediate situation with a fast rate of activation and good stability was achieved with a liquid N-caprolactam (NACL) activator. The third compound, N-acetylsuccinimide (N-ASU) showed a behavior similar to that of N-OSU.

Both N-acetyl and N-acetoxy succinimides, while being rapid acetylants as already said, show poor stability under standard storage conditions. Thus, N-acetylcaprolactam was selected as the best activator.

As disclosed in the patent to Kralovic, acetyl salicylic acid was found to be a compound to be regarded as a "weak acetylating agent". Such compound is used to keep the peracetic acid concentration at an as constant as possible level in bleaching powdered formulations including perborate and acyl-donors (TAED, TAGU (tetraacetylglycouril)).

Thus, the need was felt of formulating activators simultaneously containing a fast rate acetylating agent such as acetylcaprolactam, and a weak acetylating agent such as acetylsalicilic acid. The presence of acetylsalicilic acid in the activator assists in decreasing the pH value of the activated solution, thereby promoting its stabilization.

The preparation of the various compounds in order to find that one having the most suitable activating and stability with time features was carried out on the basis of a precise rationale.

Attention was first devoted to the search for a generator that meets the requirements listed below in decreasing order of decreasing importance:

1. A greater better stability in terms of pH and $H_2O_2$ (hydrogen peroxide=, peroxide anion source) of the solution stored at different temperatures (25° C., 30° C., 40° C.) as provided for by the premature aging protocol of the CPMP/QWP/556/96 European Guidelines.

2. lowering solution pH, following addition of the activator itself and thus obtaining greater stability of the peracetic acid concentration with time. In order to check the first parameter or requirement, pH values of parent solutions having different compositions and stored at the same temperature were monitored against time. This parameter was in fact regarded as being sufficient to act as a stability indicator, since a decrease in the pH value is also indicative of a decrease in hydrogen peroxide concentration, that releases $H^+$ ions ($pH = \log 1/[H^+]$) into the solution, with loss of oxygen atoms, owing to a degradation by "dismutation". The composition of the different tested solutions can be summarized in the following table, where concentration ranges for each component are shown.

| | Component | % w/w |
|---|---|---|
| 1. | Deionised water (Ph. Eu.) | q.b.a 100.00 |
| 2. | Sodium phosphonate Sodium salt of HEDP-Hydroxyethylidene diphosphonic acid Tetrasodium salt of 1-dell'acido 1-hydroxyethylen-1,1-diphosphonic acid | 0.005–5.000 |
| 3. | Dibasic sodium phosphate dodecahydrate (Ph. Eu.) | 0.005–5.000 |
| 4. | Monobasic potassium phosphate (Ph. Eu.) | 0.005–5.0% |
| 5. | Monohydrate citric acid (Ph. Eu.) | 0.005–5.000 |
| 6. | Hydrogen peroxide 35% w/w | 0.500–60.00 |
| 7. | Isopropyl alcohol (Ph. Eu.) | 7.00–25.00 |

In all formulations, the composition remains more or less fixed in so far as its components are concerned, except for the stabilizing agent (2) and the buffering agents (3, 4 and 5), which can be present or not in the formulation.

In the production of the parent solution the addition sequence shown above was followed, and particular care was taken when handling 35% w/w hydrogen peroxide. A pair of safety (rubber) gloves, a face mask and safety goggles were worn.

Several solutions successfully passed this initial test. The feature that was shown to be common to them was that, for the purpose of a greater stability, it was necessary to provide a stabilizing agent chosen from phosphonic acids and/or their salts. In fact, metal ions such as iron, manganese and copper (normally present as impurities of some starting raw materials such as purified water) catalyze the decomposition of hydrogen peroxide. Very low levels (even lower than 1 ppm) of these metals can catalyze the reaction. Phosphonic acids and their respective salts are excellent chelating agents that provide stabilization of peroxide systems kept on the storage vessels.

In order to be able to assess the second requirement, the solutions that had successfully passed the previous testing step were respectively activated by means of different activator solutions.

| | Component | % w/w |
|---|---|---|
| 1. | N-acetylcaprolactam | 10.0–80.0 |
| 2. | Tween 20 | 0.50–5.00 |
| 3. | Dowanol (mixture of etherified glycols) | 0.50–15.00 |
| 4. | Glycerin (Ph. Eu.) | 0.50–15.00 |
| 5. | Tartrazine yellow dye (E102) | 0.0001–0.2000 |
| 6. | Acetylsalicilic acid (Ph. Eu.) | 0.50–25.00 |
| 7. | Anhydrous (poly, mono) carboxylic acid (e.g. anhydrous citric acid) (Ph. Eu.) | 0.001–25.00 |
| 8. | Isopropyl alcohol (Ph. Eu.) | 5.00–50.00 |

The amounts and types of the tested activating compositions are in the general formulation shown below:

Important components for the activating formulations are the first, the second, the third, the fifth, and the eighth.

The presence of acetylsalicilic acid (sixth component) has two functions. First of all, it is a slow rate acetyl donor and is then a monocarboxylic acid, both functions being suitable for keeping the peracetic acid concentration stable with time. The anhydrous organic acid (seventh component), on the other hand, has the function of lowering the pH in the parent solution immediately after activation. The extent to which reduction takes place is mainly a function of the concentration of that component. It is possible to find and try different combinations of these bottom two compounds. It is possible to find and try a countless number of combinations of these two compounds so that more or less stable solutions activated at a faster or slower rate can be obtained (while keeping the other conditions unchanged).

When preparing the activating agent, particular care was taken to prevent any contact with water, and the more so with air moisture, from taking place. Thus, all the equipment used was perfectly dry and the environmental conditions were kept under strict control, above all in so far as air moisture was concerned.

In order to better proceed with the preparation, the dye as well as the acetylsalicilic acid and/or the anhydrous organic acid were previously dissolved in the mixture comprising isopropanol, glycerine, etherified glycol and surfactant. The mixing time was particularly long.

After a long selection process aimed at finding the best binary system (generator+activator), or, in other words:

the parent solution, selected from stable solutions during storage, that simultaneously allows a gradual lowering of the pH following addition of the activator to take place, so that as small as possible degradation of peracetic acid with time is obtained, and the activator is suitable for promoting lowering of the parent solution pH and at the same time for prolonging in a new manner the stability of the activated solution, owing to the simultaneous presence of a fast-rate acyl donating agent (N-acetylcaprolactam) and a slow rate acyl donating agent (acetyl salicilic acid) as well as an accurately dosed amount of anhydrous organic acid. [Increasing stability with time means keeping its physical-chemical, operating (e.g. as a bleaching agent) and microbiological features with time].

The system that was found to widely fulfil the above listed requirements is that specified in the following composition:

| Generator - Parent solution | | |
|---|---|---|
| Component | | % w/w |
| 1. Deionised water (Ph. Eu.) | | q.b.a 100.00 |
| 2. Sodium phosphonate Sodium salt of HEDP-Hydroxyethylidene diphosphonic acid) Tetrasodium salt of 1-hydroxyethylene-1,1-diphosphonic acid | | 0.450 |
| 3. Dibasic sodium phosphate dodecahydrate (Ph. Eu) | | 0.350 |
| 4. Hydrogen peroxide 35% w/w | | 12.86 |
| 5. Isopropyl alcohol (Ph. Eu.) | | 15.00 |

Specific weight: 0.985 g/ml

PH: 7–7.40 at 20.0° C.

The above solution was subjected to premature aging at 30°, 40° C. and showed a constant pH in the range from 7.00 to 7.40 over a 6 month observation period. The sample kept in a thermostat for one year was proper evidence of the ability of the parent solution.

The accurately weighed quantities of the stabilizing and buffer system (second and third components) is that showing the best performance of the activated system.

| Activator | |
|---|---|
| Component | % w/w |
| N-acetylcaprolactam | 58.500 |
| Tween 20 | 1.487 |
| Dowanol (mixture of etherified glycols) | 1.500 |
| Glycerin (Ph. Eu.) | 3.000 |
| Tartrazine yellow dye (E102) | 0.013 |
| Acetylsalicilic acid (Ph. Eu.) | 11.000 |
| Anhydrous citric acid (Ph. Eu.) | 4.500 |
| Isopropyl alcohol (Ph. Eu.) | 20.000 |

Specific weight: 0.972–0.985 g/ml

The ratio of the amounts (volume) of these two components was 14 ml activator in 1 liter of solution.

This combination was assessed several times for fast-rate activation and stability with time.

1. Once it was activated, the solution was used in repeated high level disinfection, as well as in cold-chemical sterilization processes, both by a manual procedure, i.e. by simple immersion in a vat (see FIG. 4), and by an automated procedure, i.e. resorting to a cyclically operating endoscope washing machine (see FIG. 3). In the search study carried out, it was observed that the major active principle, i.e. "Peracetic Acid" is strongly affected by the shaking action generated by the machine. The same solution, which kept its physical and chemical and microbiological features for at least 12 days while being used in a washing machine, had a stability that was markedly greater and extending to at least 60 days when used in a vat.

Figure 3:
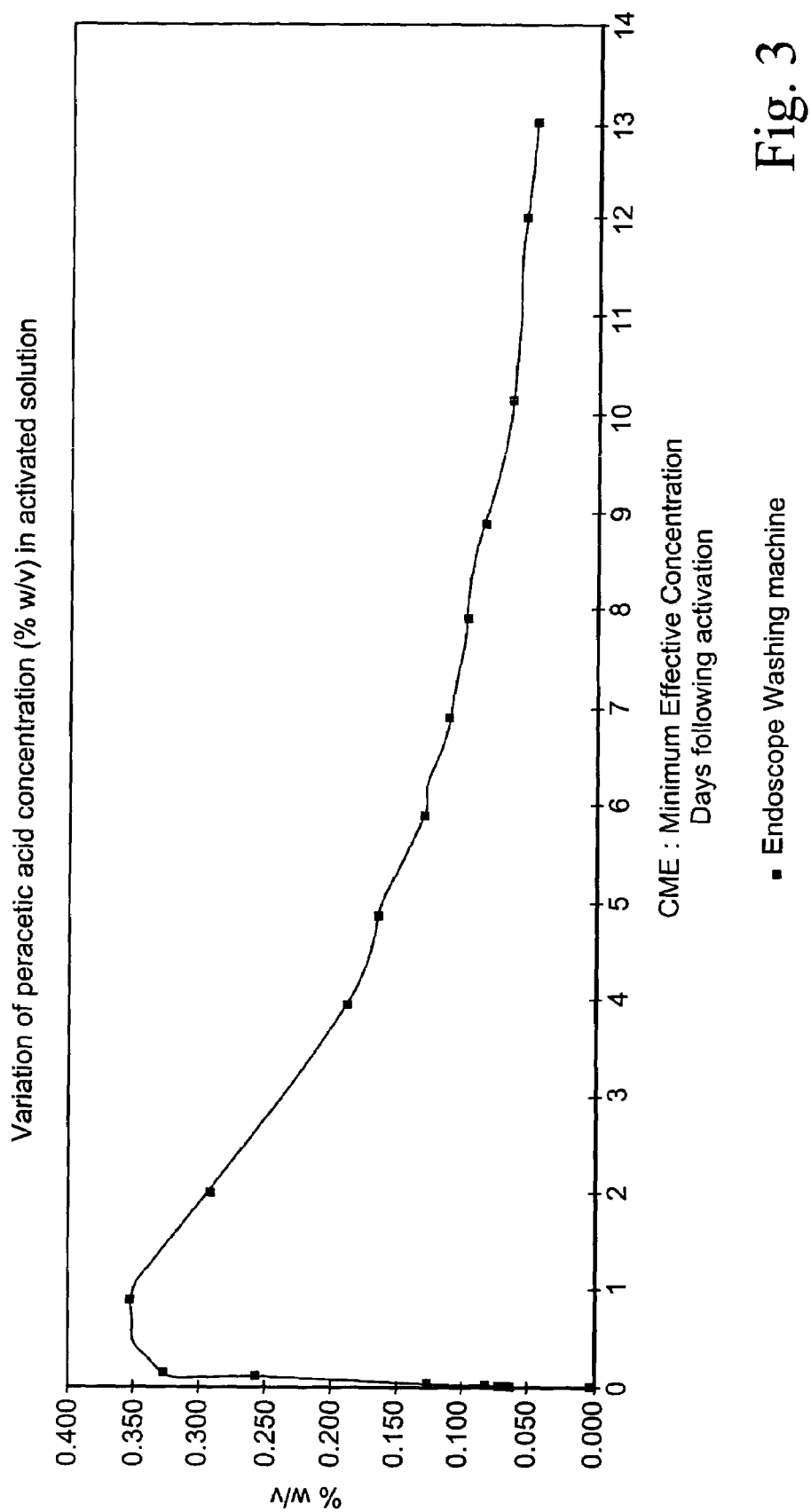
FIG. 3 is a graph comparing variation of PAA concentration over time related to minimum effective concentration in an endoscope washing machine.
Figure 4:
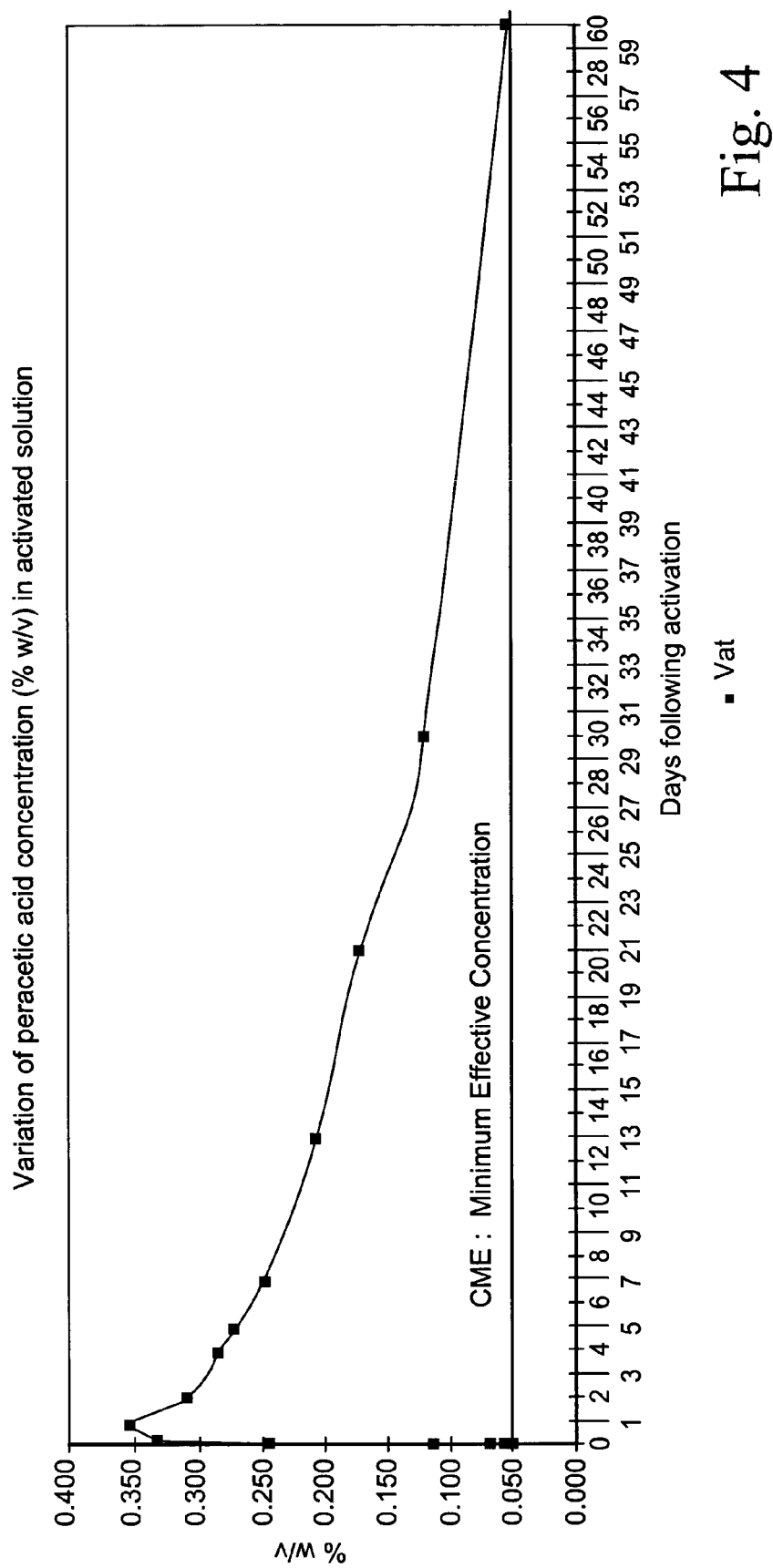
FIG. 4 is a graph comparing variation of PAA concentration in a vat over time following activation.

In the search study carried out with an endoscope washing machine, the solution was used by operating 10 full daily cycles of high-level disinfection or, better, cold-chemical sterilization for a total of 120 cycles. The contact time set for the sterilization step was 30 minutes. The variation of % w/v concentration of peracetic acid over the entire study period is shown in FIG. 3. As it will be noted, immediately after activation, the concentration increases at a fast-rate, overcomes the minimum effective concentration level (Minimum Effective Concentration Level =CME) equal to 0.05% w/v just after 15–20 minutes and reaches a maximum value equal to 0.35% w/v after 24 hours. During the following days, concentration decreases slowly down to a minimum effective level below which the effectiveness set forth below is not provided any longer. This threshold level (CME) was fixed and defined by means of the minimum % concentration of peracetic acid at which a sporicidal activity is still detected over a contact time of 15 minutes.

The surprisingly fast activation and remarkable stability simultaneously observed in one product is thought to be substantially the result of two factors combined together in the present invention:

1. An amount accurately dosed as a function of the composition of the activator in the buffer system of the stabilizing phosphonic acid-phosphonate in the parent solution.
2. Simultaneous presence in the same activating agent at a well-defined ratio of a fast-rate acyl donor (N-acetylcaprolactam) and of a slower rate acetyl donor (acetyl salicilic acid). The ratio between one of these two components and the other can be varied depending on whether one wishes fast-rate activation, or stability with time to prevail.

The activated product and, at the end of its duration, i.e. at the Minimum Effective Concentration (CME) fixed in accordance with what was described above, was subjected to biocidal activity tests necessary for classifying it as a high-level disinfectant or, better a "cold-chemical sterilizing agent". Such tests were carried out under different operating conditions and following the protocols indicated by the European Standards concerning biocidal activity.

TABLE 1

Basic Bactericidal Activity of the Oxyster Plus Long Life Liquid Disinfectant with a Contact Time of 10 minutes (according to the EN 1040 standard)

| Microorganism group | Specific strain | Suppression |
|---|---|---|
| Vegetative bacteria | *Staphylococcus aureus* ATCC 6538 | $>10^5$ |
| | *Pseudomonas aeruginosa* ATCC 15442 | $>10^5$ |

TABLE 2

Basic Tubercolicidal Activity of the Oxyster Plus Long Life Liquid Disinfectant with a Contact Time of 10 minutes (according to the EN 1040 standard).

| Microorganism group | Specific strain | Suppression |
|---|---|---|
| Acid resistant bacillus | *Mycobacterium smegmatis* ATCC 19420 | $>10^5$ |

TABLE 3

Bactericidal Activity of the Oxyster Plus Long Life Liquid disinfectant under "Clean and Dirty Conditions" with a Contact Time of 10 minutes (according to the EN 1276 standard).

| Microorganism group | Specific strain | Suppression |
|---|---|---|
| Vegetative bacteria | *Staphylococcus aureus* ATCC 6538 | $>10^5$ |
| | *Escherichia coli* ATCC 10536 | $>10^5$ |
| | *Pseudomonas aeruginosa* ATCC 15442 | $>10^5$ |
| | *Enterococcus hirae* ATCC 10541 | $>10^5$ |

TABLE 4

Tubercolicidal Activity of the Oxyster Plus Long Life Liquid Disinfectant under Clean and Dirty Conditions with a Contact Time of 10 Minutes (according to the EN 1276 standard).

| Microorganism group | Specific strain | Suppression |
|---|---|---|
| Acid resistance bacillus | *Mycobacterium smegmatis* ATCC 19420 | $>10^5$ |

TABLE 5

Basic Fungicidal Activity of the Oxyster Plus Long Life Liquid Disinfectant under "clean and dirty conditions" with a Contact Time of 10 minutes (according to the EN 1275 standard).

| Microorganism group | Specific strain | Suppression |
|---|---|---|
| Fungi at the vegetative and spore states | *Candida albicans* ATCC 10231 | $>10^4$ |
| | *Aspergillus niger* ATCC 16404 | $>10^4$ |

TABLE 6

Fungicidal Activity of the Oxyster Plus Long Life Liquid disinfectant under "clean and dirty conditions" with a Contact Time of 10 minutes (according to the EN 1650 standard).

| Microorganism group | Specific strain | Suppression |
|---|---|---|
| Fungi at the vegetative and spore states | *Candida albicans* ATCC 10231 | $>10^4$ |
| | *Aspergillus niger* ATCC 16404 | $>10^4$ |

TABLE 7

Basic Sporicidal Activity of the Oxyster Plus Long Life liquid Disinfectant with a Contact Time of 15 minutes (according to the NFT 72-230 standard).

| Microorganism group | Specific strain | Suppression |
|---|---|---|
| Bacterial Spores | *Bacillus subtilis* var. *niger* ATCC 9372 | $>10^5$ |
| | *Bacillus cereus* CIP 7803 | $>10^5$ |
| | *Clostridium sporogenes* CIP 7939 | $>10^5$ |

TABLE 8

Bactericidal, Fungicidal and Sporicidal Activities by the "germ-carrier method" with the Oxyster Plus Long Life disinfectant (according to the AFNOR NF T 72-190 standard (1988).

| Standard microorganism strains | Suppression | Contact time |
|---|---|---|
| *Pseudomonas aeruginosa* ATCC 15442 | $>10^5$ | 10 minutes |
| *Escherichia coli* ATCC 10536 | $>10^5$ | |
| *Staphylococcus aureus* ATCC 6538 | $>10^5$ | |
| *Enterococcus hirae* ATCC 10541 | $>10^5$ | |
| *Aspergillus niger* ATCC 16404 | $>10^4$ | 20 minutes |
| *Candida albicans* ATCC 10231 | $>10^4$ | 10 minutes |
| *Mycobacterium smegmatis* ATCC 19420 | $>10^5$ | 10 minutes |
| Spores of *Bacillus subtilis* var. *niger* ATCC 9372 | $>10^3$ | 15 minutes |
| Spores of *Clostridium sporogenes* CIP 7939 | $>10^3$ | |
| Spores of *Bacillus cereus* CIP 7803 | $>10^3$ | 30 minutes |

TABLE 9

Sporicidal Activity of the Oxyster Plus Long Life Liquid Disinfectant under "Clean and Dirty conditions" with Contact Time of 15–30 minutes (according to the NFT 72-300 standard).

| Microorganism group | Specific strain | Contact time | Suppression |
|---|---|---|---|
| Bacterial spores | Bacillus subtilis var. niger ATCC 9372 | 15 minutes | >$10^3$ |
| | Clostridium sporogenes CIP 7939 | | >$10^3$ |
| | Bacillus cereus CIP 7803 | 30 minutes | >$10^3$ |

TABLE 10

Virus Inactivation by Oxyster Plus Long Life at a temperature of 20° C.

| Organisms | Lethality (minutes) |
|---|---|
| HBV in the presence of 33% blood | 1 |
| HCV in the presence of 33% blood | 1 |
| HIV in the presence of 33% blood | 1 |

The HIV, HBV and HCV viruses are inactivated in very short times in the presence of contaminating organic material (33% blood).

The present invention differs from the disclosure made by Bansemir in that it exploits the combined effect of a ternary system consisting of hydrogen peroxide in stoichiometric excess with respect to the stoichiometric amount of the other reaction component, peracetic acid and alcohol, whose enhanced biocidal effect as experimentally tested by the inventors (see the following Table) was neither disclosed nor taken advantage of in the prior art. These three components in different combinations with respect to each other were subjected to a sporicidal activity test with the *Bacillus subtilis* ATCC 9372 standard strain according to the NFT 72-231 standard.

| Contact times | 2 mins | 5 mins | 15 mins | 30 mins |
|---|---|---|---|---|
| 1 FORMULATION peracetic acid 0.05% w/w | + | + | + | − |
| 2 FORMULATION peracetic acid 0.05% w/w + isopropyl alcohol 10.00% w/w | + | + | − | − |
| 3 FORMULATION peracetic acid 0.05% w/w + hydrogen peroxide 3.00% w/w | + | − | − | − |
| 4 FORMULATION hydrogen peroxide 3.00% w/w + isopropyl alcohol 10.00% w/w | + | + | + | + |
| 5 FORMULAZIONE peracetic acid 0.05% w/w + hydrogen peroxide 3.00% w/w + isopropyl alcohol 10.00% w/w | − | − | − | − |

+ = growth (no activity)
− = no growth (activity)

By bearing then in mind a combination disclosed in the patent to Kralovic with the patent to Bansemir, it will be noted that while with the method disclosed by Kralovic the synergistic effect due to the triple component cannot be exploited, in the method according to the present invention, just owing to the liquid state of one of the two components of the system (parent solution) it is possible to obtain a synergistic biocidal effect owing to the addition of a desired percentage of alcohol to the parent solution.

The present invention is susceptible to numerous modifications and variations without departing the scope and spirit of the invention as defined by the Claims.

The invention claimed is:

1. A system for a fast-rate preparation just before use of organic peroxyacids, in a hydroalcoholic environment, by mixing at a temperature lower than 40° C., a first reactant and a second reactant, kept separate from each other during storage, to obtain an activated solution, wherein:
said first reactant is an activator in solid or liquid state at a temperature from 5° C. to 45° C., is lipophilic, and comprises at least one acyl donating group, and
said second reactant is in liquid state, at least in the temperature range from 5° C. and 40° C., is hydrophilic, and comprises a peroxide anion source in a concentration such as to provide at least 10-fold molar excess of peroxide with respect to the stoichiometric amount of said at least one acyl-donor, a biocidal agent comprising at least one $C_1$–$C_{18}$ linear or branched aliphatic and/or aromatic alcohol, and a stabilizing buffer component suitable for keeping said second reactant at a desired pH value.

2. A system as claimed in claim 1, wherein said acyl-donor comprises a compound having the following general formula:

$R^1$—CO—L

where L is a leaving group and $R^1$ is an alkyl, aralkyl or aryl group, each group having up to 24 carbon atoms and being either substituted or unsubstituted.

3. A system as claimed in claim 2, wherein said acyl-donor comprises an N-acyl donor having general formula:

$R^1$—CO—L

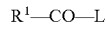

where L is a leaving group bonded to a carbonyl carbon through a nitrogen atom.

4. A system as claimed in claim 3, wherein said acyl-donor comprises an O-acyl donor having general formula:

$R^1$—CO—L

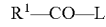

where L is a leaving group bonded to a carbonyl carbon through an oxygen atom.

5. A system as claimed in claim 2, wherein said acyl-donor is selected from the group consisting of acetyl salicylic acid, N-acetoxysuccinimide, N-acetylsuccinimide, N-acetylcaprolactam, N,N, N,N-tetraacetykethylethyldiamine (TAED), N,N, N-triacetylethylenediamine and acetylated sugars.

6. A system as claimed in claim 1, wherein the amount of said acyl donating group is in the range from 0.01% to 100.00% as a function of the percentage w/w of peroxide to be obtained, and of the quantitative ratio of said second reactant to said first reactant.

7. A system as claimed in claim 1, wherein said first reactant comprises at least one solvent or dispersant, when in the liquid state.

8. A system as claimed in claim 7, wherein said solvent comprises a branched chain alcohol.

9. A system as claimed in claim 8, wherein said branched chain alcohol is selected from higher $C_5$–$C_{18}$ alcohols and lower $C_1$–$C_4$ alcohols.

10. A system as claimed in claim 7, wherein the amount of said at least one solvent or dispersant is in the range from 5.00% w/w to 50.00% w/w.

11. A system as claimed in claim 1, wherein said activator comprises a dye that withstands the bleaching action of peroxyacids to act as a visual indicator of completed mixing of said first reactant with said second reactant throughout the stability duration of the system.

12. A system as claimed in claim 1, wherein either said first reactant, when in the liquid state, or said second reactant, comprises a non-ionic surfactant and/or a solvating agent.

13. A system as claimed in claim 12, wherein the amount of non-ionic surfactant component and/or solvating agent is proportional to the amount of acyl donor to be dispersed in said second reactant.

14. A system as claimed in claim 13, wherein the concentration of said non-ionic surfactant is in the range from 0.0001% w/w and 5.00% w/w.

15. A system as claimed in claim 13, wherein said non-ionic surfactant is from the group consisting of ethoxylated alcohol, and a Tween-sorbitan monolaurate, monooleate, monostearate polyethoxylate having an HLB value higher than 7.

16. A system as claimed in claim 13, wherein said solvating agent comprises a glycol ether.

17. A system as claimed in claim 16, wherein said glycol ether is selected from the group consisting of hexylene glycol, diethylene glycol monohexyl ether, and tripropylene glycol methyl ether.

18. A system as claimed in claim 16, wherein the concentration of said glycol ether is in the range from 0.0001% w/w and 5.00% w/w.

19. A system as claimed in claim 1, wherein said peroxide anion source within said second reactant comprises hydrogen peroxide ($H_2O_2$) in an amount in the range from 0.001% w/w to 60% w/w.

20. A system as claimed in claim 1, wherein the concentration of said biocidal agent is in the range from 5.00% w/w to 70.00% w/w.

21. A system as claimed in claim 1, wherein said stabilizing buffer component comprises at least a phosphate or a phosphonate compound.

22. A system as claimed in claim 21, wherein the amount of said phosphate and/or phosphonate compound is in the range from 0.001% w/w and 20.00% w/w.

23. A system as claimed in claim 21, wherein the amount of said phosphate and/or phosphonate compound is such that said second reactant is kept at a pH above 6.5.

24. A system as claimed in claim 1, wherein said stabilizing buffer component is responsible for lowering pH of the solution obtained down to a minimum pH 3.00.

25. A system as claimed in claim 1, wherein the mixing temperature is lower than 25° C.

26. A system as claimed in claim 23, wherein the second reactant is kept at a pH of 7.0.

27. A system as claimed in claim 1, wherein the pH of the solution is lowered to a minimum of pH 4.5.

* * * * *